(12) United States Patent
Adrian et al.

(10) Patent No.: US 6,514,388 B1
(45) Date of Patent: Feb. 4, 2003

(54) METHOD FOR PRODUCING HIGHLY PURE MONOETHYLENE GLYCOL

(75) Inventors: Till Adrian, Bobenheim-Roxheim (DE); Bernd Bessling, Grünstadt (DE); Hans Hasse, Kaiserslautern (DE); Frans Vansant, Kalmthout (BE); Gerhard Theis, Maxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/744,433

(22) PCT Filed: Sep. 21, 1999

(86) PCT No.: PCT/EP99/06967

§ 371 (c)(1),
(2), (4) Date: Jan. 24, 2001

(87) PCT Pub. No.: WO00/17140

PCT Pub. Date: Mar. 30, 2000

(30) Foreign Application Priority Data

Sep. 23, 1998 (DE) .......................... 198 43 652

(51) Int. Cl.$^7$ .......................... B01D 3/00; C07C 29/76; C07C 29/80
(52) U.S. Cl. .......................... 203/18; 203/73; 203/79; 203/80; 568/868
(58) Field of Search .......................... 203/18, 79, 91, 203/80, 87, 73; 568/867, 868, 916

(56) References Cited

U.S. PATENT DOCUMENTS

| 3,847,754 | A | * | 11/1974 | Oliver .......................... 203/71 |
| 4,349,417 | A | | 9/1982 | Rebsdat et al. ................ 203/33 |
| 4,622,104 | A | | 11/1986 | Néel et al. ..................... 203/18 |
| 6,133,489 | A | | 10/2000 | Mohr et al. ................. 568/914 |

FOREIGN PATENT DOCUMENTS

| CA | 1 330 350 | 6/1994 |
| DE | 1 942 094 | 2/1973 |
| DE | 33 38 488 | 5/1984 |
| DE | 196 02 116 | 7/1997 |
| EP | 032 665 | 7/1981 |
| GB | 1257558 | 12/1971 |
| JP | 6 0089 439 | 10/1983 |

* cited by examiner

Primary Examiner—Virginia Manoharan
(74) Attorney, Agent, or Firm—Keil & Weinkauf

(57) ABSTRACT

A process for the distillative recovery of high purity monoethylene glycol from the hydrolysis product of ethylene oxide by pressure dewatering, vacuum dewatering and subsequent purifying distillation, which includes the pressure dewatering columns or at least the first pressure dewatering column of the battery (2, 3, 4) having a stripping section with at least one separating stage, preferably with from 2 to 10 separating stages, particularly preferably with from 3 to 6 stages, and a portion of the overhead stream of the pressure dewatering column(s) (2, 3, 4) having a stripping section being removed from the system.

12 Claims, 3 Drawing Sheets

PRIOR ART

METHOD FOR PRODUCING HIGHLY PURE MONOETHYLENE GLYCOL

Figure 1:
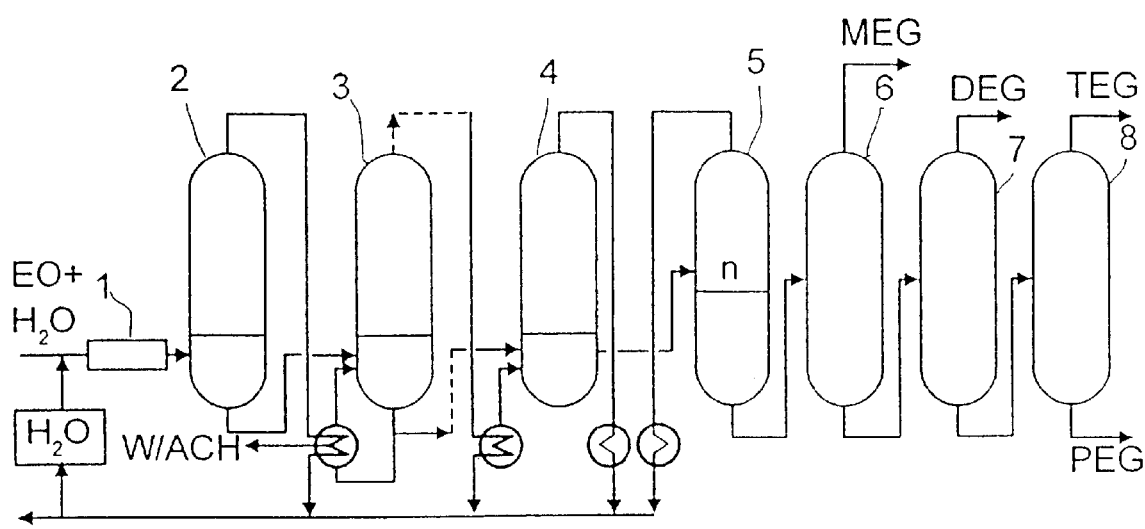

This invention relates to a process for producing high purity monoethylene glycol.

Monoethylene glycol is industrially produced by hydrolysis of ethylene oxide, dewatering and purifying distillation. To improve the selectivity of the ethylene oxide (hereinafter abbreviated to EO) hydrolysis, the hydrolysis reactor is operated using a large excess of water (water:EO weight ratio=4:1 to 15:1). This makes it possible to suppress the fraction of higher glycols, especially diethylene glycol, triethylene glycol, etc. The hydrolysis reactor is customarily operated at temperatures of 120 to 250° C. and pressures of 30–40 bar. The hydrolysis product is initially dewatered, to a residual water content of 100–200 ppm, and then separated into the various glycols in pure form.

The dewatering is generally carried out in a battery of pressure-graduated columns, with decreasing pressure. For heat integration reasons, generally only the bottoms reboiler of the first pressure column is heated with external steam, whereas all the other pressure columns are heated with the vapors from the preceding column. The feed enters each column at a point below the first plate, since no stripping section is required to separate water and glycols. Depending on the water content of the hydrolysis reactor effluent and on the pressure/temperature level of the external steam used in the first column's bottoms reboiler, the pressure dewatering battery comprises from 2 to 7 columns. The pressure dewatering stage is followed by a vacuum dewatering stage, which generally takes place in a column equipped with a stripping section. The water obtained from the dewatering is returned to a point upstream of the hydrolysis reactor. The dewatered solution of glycols is separated into the pure materials in a plurality of columns. Monoethylene glycol, diethylene glycol and triethylene glycol are each withdrawn as top-of-column product, while all other higher glycols are obtained in the form of a mixture known as polyethylene glycols as the bottom product of the last column.

Conventional glycol plants, in addition to the product streams, customarily have only a further single outlet, the acetaldehyde purge at the bottoms reboiler of the second pressure dewatering column. There, the uncondensed fraction of the first column's vapors used for heating is removed from the system. Thus, secondary components, either carried into the glycol plant by the water/EO stream or formed in the glycol plant as a consequence of secondary reactions, can only be removed from the system via the acetaldehyde purge or via the product streams. The latter impairs product quality and so is undesirable.

Hitherto, glycol plants were optimized only with regard to their principal functions, especially energy and capital costs reduction for the dewatering and purifying distillation. Of late, increasingly tougher requirements are being placed on the product quality of monoethylene glycol, especially with regard to the level of secondary components. There are two monoethylene glycol product qualities: technical grade (antifreeze grade) with lower requirements, for use as coolant, and fiber grade, with strict requirements for use in fiber manufacture. The exact specification of fiber grade varies with the customer, but for free aldehydes, reckoned as acetaldehyde, spectrophotometrically assayed as blue MBTH complex, it generally envisages the range from 7 to 20 ppm and for the minimum UV transmission it generally envisages 76%–80% at 220 nm and 90%–95% at 275 nm. The contributors to the free aldehydes measurement are in particular formaldehyde, acetaldehyde and glycolaldehyde.

The UV-active substances, known as UV spoilers, are largely unknown, but are specification-destructive even in concentrations of less than 1 ppm. Examples are acrolein and crotonaldehyde.

JP-A-60,089,439 describes a process for purifying monoethylene glycol by vacuum distillation with a supply of inert gas. The nitrogen stream strips out most of the secondary components to leave a high purity glycol which is suitable for fiber manufacture. However, the process has the disadvantage that large amounts of nitrogen are needed for effective removal of secondary components. This leads to undesirable product losses in the exit gas and to an excessively large fluid-dynamic stress on the distillation column.

DE-A-1 942 094 describes a process for purifying monoethylene glycols by steam distillation in a stripping column, the steam increasing the volatility of the impurities with regard to monoethylene glycol.

CA-C-133050 describes a process for purifying monoethylene glycol by addition of bisulfite ions and subsequent treatment with anion exchange resins.

There are also purification processes for monoethylene glycol where the formation of secondary components is said to be reduced by special measures in the area of apparatus construction and the materials of construction used for the apparatus. DE-A-19602116 describes a purification process for monoethylene glycol in an apparatus whose surface has been treated with reducing phosphorus compounds. However, the abovementioned processes have the disadvantage of requiring additives or additional equipment-based measures to recover high purity monoethylene glycol.

It is an object of the present invention to provide a simple distillative process for recovering high purity monoethylene glycol, without the use of additives or of specific materials of construction. Specification-destructive secondary components are to be removed from the system in predominantly aqueous waste streams having glycol contents of not more than 1% by weight and the secondary components in the waste streams are to be concentrated by a factor of 10–100, since too much wastewater is produced otherwise.

We have found that this object is achieved by a process for the distillative recovery of high purity monoethylene glycol from the hydrolysis product of ethylene oxide by pressure dewatering, preferably in a battery, vacuum dewatering and subsequent purifying distillation, which comprises the pressure dewatering taking place in a dewatering column having a stripping section with at least one separating stage, particularly preferably with from 2 to 10 separating stages, particularly preferably with from 3 to 6 stages, and a portion of the overhead stream of the dewatering column(s) having a stripping section being removed from the system.

It was determined that removal of specification-destructive secondary components is particularly effective at certain locations in the process. Identifying these locations in the process is not a trivial matter, since the complex phase equilibria have hitherto made it impossible to arrive at a sufficiently confident assessment of the behavior of the secondary components. For this reason, conventional large industrial processes have only a very coarse outlet for extremely low boiling secondary components, the acetaldehyde purge at the bottoms reboiler of the second pressure dewatering column. This outlet is not optimized, since the behavior of the secondary components was largely unknown and was not taken into account at the process design stage.

The components are herein subdivided into three classes with regard to their boiling range:

1. low boilers, having a volatility below that of water (especially acetaldehyde, formaldehyde in pure water, acrolein)

2. medium boilers having a volatility between that of water and monoethylene glycol (especially formaldehyde in glycol-containing aqueous solutions, formaldehyde in anhydrous monoethylene glycol, glycolaldehyde, crotonaldehyde)
3. high boilers having a lower volatility than monoethylene glycol (especially relatively high molecular weight aldehydes, UV spoilers).

According to the invention, the removal of secondary components, especially low boilers, in the pressure dewatering stage is improved. To this end, the pressure dewatering column or at least the first pressure dewatering column of the battery has a stripping section with at least one separating stage, preferably with from 2 to 10 separating stages, particularly preferably with from 3 to 6 stages, and a portion of the overhead stream of the pressure dewatering column(s) having a stripping section is removed from the system.

Conventional large industrial processes utilize an acetaldehyde purge at the bottoms reboiler of the second pressure dewatering column: this is where the vapors of the first pressure dewatering column are substantially condensed, with the uncondensed fraction, about 1–5% by weight of total vapors, being removed from the system. The remaining vapors may, if desired, be postcondensed in a further heat transferor, and the heat of condensation may be utilized at a suitable location in the overall process. However, this conventional solution will remove via the acetaldehyde purge only secondary components which leave the first pressure dewatering column as part of the vapors. This is inadequate in the case of formaldehyde in particular, since the volatility of formaldehyde in aqueous glycol solutions decreases with increasing glycol content, especially as a consequence of chemical reactions of the formaldehyde with water and glycols. So as to separate formaldehyde from the glycol-containing bottom product of the pressure dewatering column, the pressure dewatering column or at least the first pressure dewatering column of a battery requires a stripping section of at least one separating stage, preferably from 2 to 10 separating stages, particularly preferably from 3 to 6 separating stages. Only when the formaldehyde has been removed into the purely aqueous vapors of the first column can it be purged from the system together with acetaldehyde. The efficiency of removal of the formaldehyde in the stripping section improves with the temperature and correspondingly the pressure in the pressure dewatering column, or in the first pressure dewatering column of the battery, and with the water content of the reactor effluent. Two of the additional plates in the stripping section can be saved if the bottoms reboiler is constructed as a "divided base" as described in DE-C-3338488.

The amount of secondary components, especially acetaldehyde or formaldehyde, removed from the system depends on the amount of wastewater removed. It has to be borne in mind, however, that the amount of vapor not condensed in the bottoms reboiler of the second dewatering column cannot be increased ad infinitum for reasons of the integrated energy system and on account of control-engineering restraints. The inventors have found a particularly preferred version of the process, whereby further removal of secondary components from the condensed vapor is possible by steam stripping. The stripping steam loaded with secondary components can subsequently be utilized for its energy content at a suitable location in the process. Steam stripping, therefore, requires no additional energy, only an additional apparatus. The removal of secondary components from the system is particularly effective when the effluent from the stripper is refluxed into the first dewatering column, since this recycling will increase the aldehyde content at the top of the first pressure dewatering column and in the stripper and hence also the removal rate.

Advantageously, the temperature below the feed point is above 80° C., but preferably within the range from 100° C. to 250° C., particularly preferably within the range from 115° C. to 230° C. The pressure in the stripping section is not less than 1 bar, preferably within the range from 2 to 30 bar.

Advantageously, the overhead stream of the dewatering column(s) having a stripping section is introduced into a partial condenser and/or a stripper, especially a steam stripper, and the gaseous stream(s) enriched with the secondary components is (are) removed from the system.

Suitably, the partial condenser and/or the stripper are operated at above 90° C., preferably at from 120° C. to 250° C.

Figure 2:
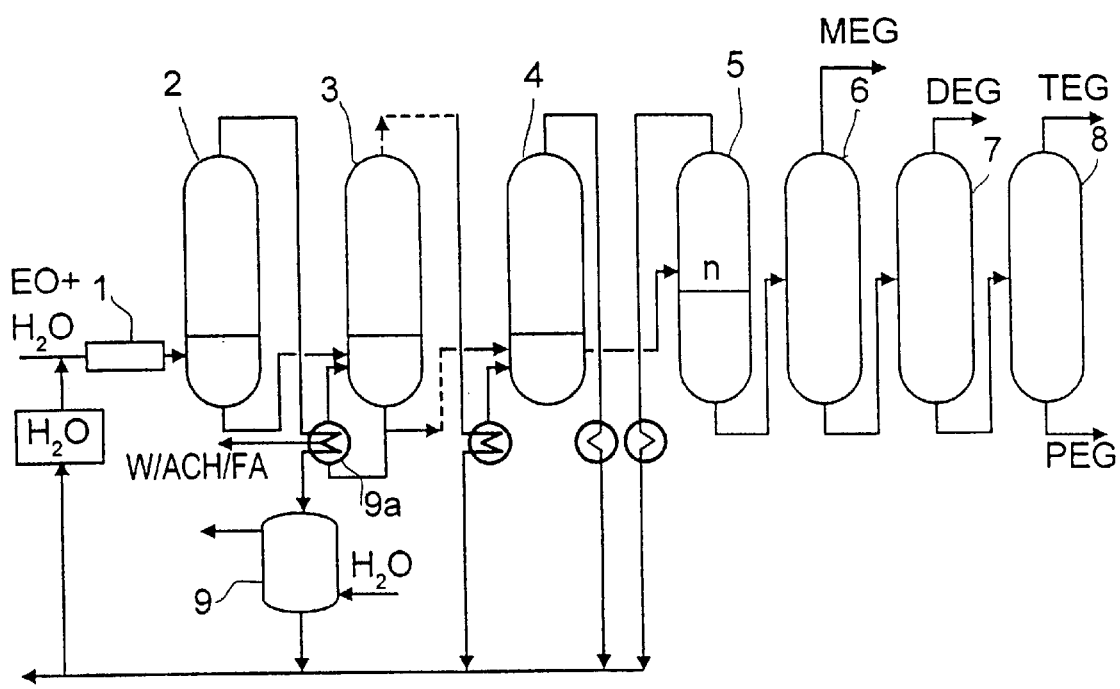
Figure 3:
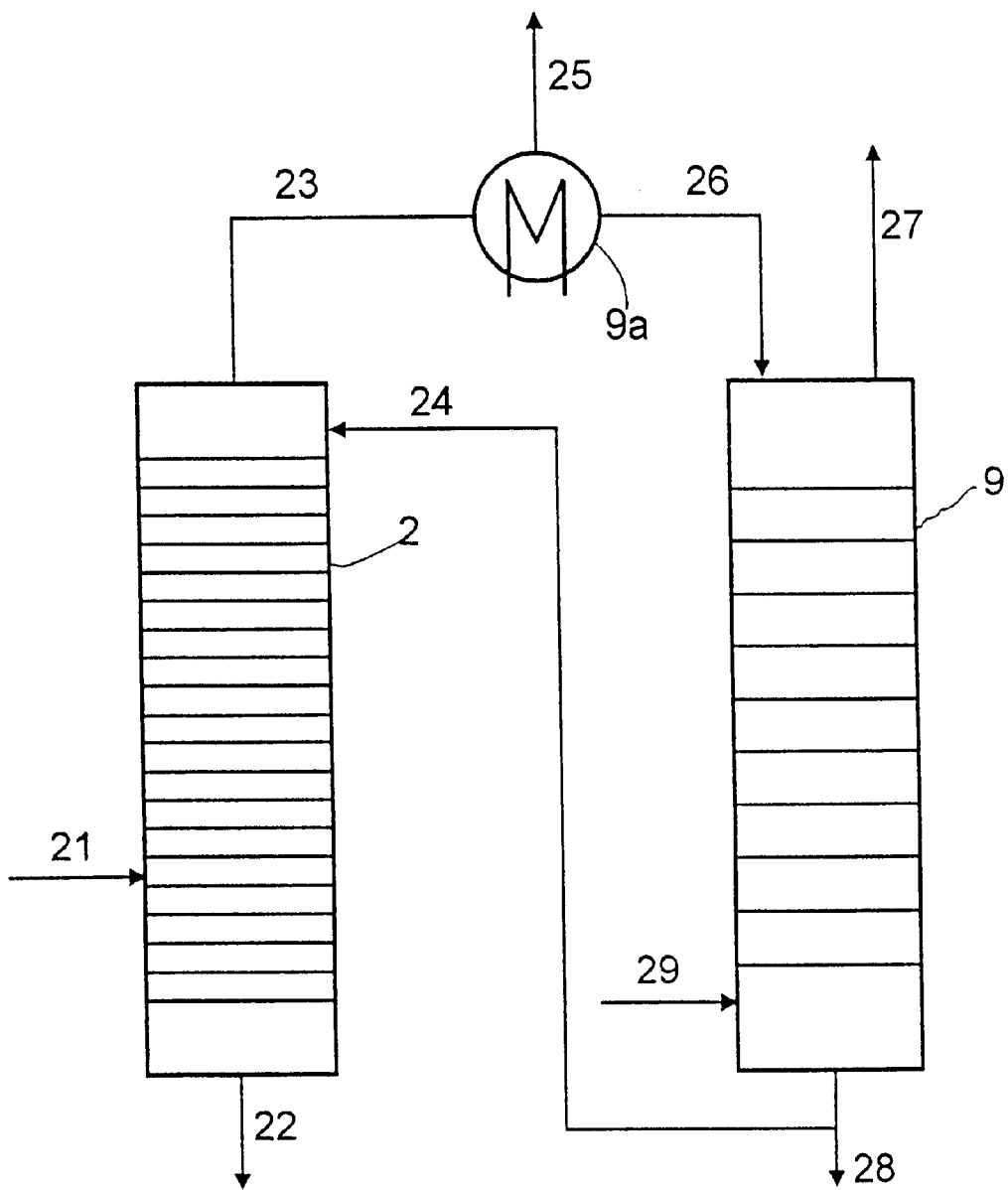

Embodiments of the invention will now be more particularly described by way of example with reference to a drawing, where FIG. 1 shows a scheme for a large industrial process for glycol recovery according to the prior art, FIG. 2 shows a scheme of a particularly preferred process for glycol recovery according to the invention, FIG. 3 shows an illustrative example of a process of the invention, featuring a pressure dewatering column with a stripping section and an outlet for secondary components as overhead stream and also subsequent concentrating in a partial condenser and a stripper.

FIG. 1 shows a scheme for the large industrial recovery of glycol according to the prior art. A water/ethylene oxide mixture having a water:ethylene oxide weight ratio of from 4:1 to 15:1 is fed to the hydrolysis reactor 1 and then to a pressure dewatering stage, herein depicted as a battery of three pressure-graduated columns 2, 3 and 4. The feed point for the columns 2, 3 and 4 is located in the bottom region in each case. The vapor stream from the first pressure dewatering column 2 is condensed in the bottoms reboiler of the second pressure dewatering column 3 and the uncondensed fraction is removed from the system as so-called acetaldehyde purge (W/ACH, i.e., water/acetaldehyde). The condensed vapors from the pressure dewatering columns 2, 3 and 4 are returned to a point upstream of the hydrolysis reactor 1. The bottom stream from the last pressure dewatering column 4 is introduced into the middle section of a vacuum dewatering column 5. The predominantly water-containing vapor from the vacuum dewatering column 5 is likewise condensed and returned to a point upstream of the hydrolysis reactor 1. The bottom effluent from the vacuum dewatering column 5 is fed to a monoethylene glycol purifying distillation column 6, from where monoethylene glycol plus secondary components, especially formaldehyde, glycolaldehyde and UV spoilers, are withdrawn as top product. The bottom effluent from the monoethylene glycol purifying distillation column 6 is fed to a diethylene glycol purifying distillation column 7, from which pure diethylene glycol is withdrawn as top product and whose bottom effluent is fed to a further column, the triethylene glycol purifying distillation column 8. The top product from the triethylene glycol purifying distillation column is pure triethylene glycol and the bottom effluent from the column 8 contains a mixture of higher glycols, known as polyethylene glycol.

FIG. 2, in contrast, shows a large industrial process for recovering high purity monoethylene glycol according to the invention. Compared with the process scheme of FIG. 1, the feed is introduced into the first pressure dewatering column 2 at a higher point along the length of this column, and this pressure dewatering column 2 has a stripping section of from 2 to 6 plates.

A further difference to the process of FIG. 1 is that the vapor from the first pressure dewatering column 2, following a partial condensation in the bottoms reboiler of the pressure dewatering column 3, is steam-stripped free of secondary components in a stripper 9. The stripper effluent is a gaseous stream of secondary components (W/ACH/FA, i.e., water/acetaldehyde/formaldehyde) which leaves the system.

FIG. 3 shows an example of the inventive modification of a pressure dewatering column 2 with stripping section and also with a stripper 9 for concentrating the secondary components prior to their being removed from the system.

The feed 21 of the glycol-containing stream to be separated is on the 5$^{th}$ plate of a pressure dewatering column 2 possessing 20 bubble cap plates. Its overhead stream 23 is, after partial condensation, introduced as stream 26 onto a stripper 9 possessing 10 bubble cap plates and stripped free of secondary components by countercurrent steam 29. The gaseous streams 25 and 27 containing secondary components are removed from the system. Part 24 of the bottom effluent of stripper 9 forms the reflux into the dewatering column 2. The composition of the streams 21–29 is recited in Table 1a for a process of the invention. For comparison, the composition of the streams 21–29 is recited in Table 1b for a process according to the prior art, i.e., with pressure dewatering column without stripping section and without stripper.

TABLE 1a

| | | Stream No. | | | | | | | | |
|---|---|---|---|---|---|---|---|---|---|---|
| | | 21 | 22 | 23 | 24 | 25 | 26 | 27 | 28 | 29 |
| | | Hydrolysis reactor effluent | Column 2 product | Column 2 vapor | Reflux | Condenser exit gas | Condensate | Stripper exit gas | Recycle water | Stripping steam |
| Total stream | kg/h | 124.38 | 84.46 | 51.891 | 11.975 | 0.8 | 51.091 | 1.531 | 39.14 | 1.5 |
| Temperature | °C. | 235 | 183 | 178 | 178 | 178 | 178 | 178 | 178 | 200 |
| | | liquid | liquid | gaseous | liquid | gaseous | liquid | gaseous | liquid | gaseous |
| Water | % by weight | 77.58 | 67.00 | 99.97 | 99.98 | 99.76 | 99.97 | 99.80 | 99.98 | 100.00 |
| Monoethylene glycol | % by weight | 18.30 | 26.96 | 0.00 | 0.00 | 0.00 | 0.00 | 0.00 | 0.00 | 0.00 |
| Diethylene glycol | % by weight | 3.25 | 4.79 | 0.00 | 0.00 | 0.00 | 0.00 | 0.00 | 0.00 | 0.00 |
| Triethylene glycol | % by weight | 0.71 | 0.20 | 0.00 | 0.00 | 0.00 | 0.00 | 0.00 | 0.00 | 0.00 |
| Tetraethylene glycol | % by weight | 0.14 | 0.00 | 0.00 | 0.00 | 0.00 | 0.00 | 0.00 | 0.00 | 0.00 |
| Acetaldehyde | % by weight | 0.00 | 0.00 | 0.01 | 0.00 | 0.14 | 0.00 | 0.11 | 0.00 | 0.00 |
| Formaldehyde | % by weight | 0.01 | 0 | 0.02 | 0.02 | 0.09 | 0.02 | 0.09 | 0.02 | 0.00 |
| Acetaldehyde | weight ppm | 26 | 24 | 64 | 10 | 1434 | 43 | 1071 | 10 | 0 |
| Formadehyde | weight ppm | 94 | 100.00 | 231 | 192 | 935 | 219 | 934 | 192 | 0 |
| Total | | 100.00 | 100.00 | 100.00 | 100.00 | 100.00 | 100.00 | 100.00 | 100.00 | 100.00 |
| Water | g/h | 96,497.1 | 56,588.2 | 51,875.7 | 11,972.6 | 798.1 | 51,077.6 | 1527.9 | 39,132.1 | 1500.0 |
| Monoethylene glycol | g/h | 22,765.3 | 22,770.1 | 0.0 | 0.0 | 0.0 | 0.0 | 0.00 | 0.0 | 0.0 |
| Diethylene glycol | g/h | 4046.5 | 4047.3 | 0.0 | 0.0 | 0.0 | 0.0 | 0.0 | 0.0 | 0.0 |
| Triethylene glycol | g/h | 883.5 | 883.7 | 0.0 | 0.0 | 0.0 | 0.0 | 0.0 | 0.0 | 0.0 |
| Tetraethylene glycol | g/h | 172.8 | 172.8 | 0.0 | 0.0 | 0.0 | 0.0 | 0.0 | 0.0 | 0.0 |
| Acetaldehyde | g/h | 3.2 | 0.0 | 3.3 | 0.1 | 1.6 | 2.2 | 1.6 | 0.4 | 0.0 |
| Formaldehyde | g/h | 11.7 | 2.0 | 12.0 | 2.3 | 1.4 | 11.2 | 1.4 | 7.5 | 0.0 |

TABLE 1b

| | | Stream No. | | | | | | | | |
|---|---|---|---|---|---|---|---|---|---|---|
| | | 21 | 22 | 23 | 24 | 25 | 26 | 27 | 28 | 29 |
| | | Hydrolysis reactor effluent | Column 2 product | Column 2 vapor | Reflux | Condenser exit gas | Condensate | Stripper exit gas | Recycle water | Stripping steam |
| Total stream | kg/h | 124.42 | 84.47 | 51.925 | 11.975 | 0.8 | 51.125 | | 39.15 | 0 |
| Temperature | °C. | 235 | 183 | 178 | 178 | 178 | 178 | 0 | 178 | |
| | | liquid | liquid | gaseous | liquid | gaseous | liquid | | liquid | |
| Water | % by weight | 77.58 | 67.00 | 99.98 | 99.98 | 99.78 | 99.98 | | 99.98 | |
| Monoethylene glycol | % by weight | 18.30 | 26.96 | 0.00 | 0.00 | 0.00 | 0.00 | | 0.00 | |
| Diethylene glycol | % by weight | 3.25 | 4.79 | 0.00 | 0.00 | 0.00 | 0.00 | | 0.00 | |
| Triethylene glycol | % by weight | 0.71 | 1.05 | 0.00 | 0.00 | 0.00 | 0.00 | | 0.00 | |
| Tetraethylene glycol | % by weight | 0.14 | 0.20 | 0.00 | 0.00 | 0.00 | 0.00 | | 0.00 | |
| Acetaldehyde | % by weight | 0.00 | 0.00 | 0.01 | 0.00 | 0.15 | 0.00 | | 0.00 | |
| Formaldehyde | % by weight | 0.01 | 0.01 | 0.02 | 0.02 | 0.07 | 0.02 | | 0.02 | |
| Acetaldehyde | weight ppm | 26 | 3 | 67 | 45 | 1508 | 45 | 0 | 45 | |
| Formaldehyde | weight ppm | 94 | 55 | 173 | 165 | 701 | 165 | 0 | 165 | |
| Total | | 100.00 | 100.01 | 100.00 | 100.00 | 100.00 | 100.00 | | 100.00 | |
| Water | g/h | 96,528.1 | 56,594.9 | 51,912.5 | 11,972.5 | 798.2 | 51,114.3 | | 39,141.8 | |
| Monoethylene glycol | g/h | 22,772.6 | 22,772.8 | 0.0 | 0.0 | 0.0 | 0.0 | | 0.0 | |
| Diethylene glycol | g/h | 4047.8 | 4047.8 | 0.0 | 0.0 | 0.0 | 0.0 | | 0.0 | |
| Triethylene glycol | g/h | 883.8 | 883.8 | 0.0 | 0.0 | 0.0 | 0.0 | | 0.0 | |
| Tetraethylene glycol | g/h | 172.8 | 172.8 | 0.0 | 0.0 | 0.0 | 0.0 | | 0.0 | |

TABLE 1b-continued

| | | Stream No. | | | | | | | | |
|---|---|---|---|---|---|---|---|---|---|---|
| | | 21 | 22 | 23 | 24 | 25 | 26 | 27 | 28 | 29 |
| Acetaldehyde | g/h | 3.2 | 0.3 | 3.5 | 0.5 | 1.2 | 2.3 | | 1.7 | |
| Formaldehyde | g/h | 11.7 | 4.6 | 9.0 | 2.0 | 0.6 | 8.4 | | 6.5 | |

The process of the invention provides for a product stream 22 being obtained from the first pressure dewatering column 2 which has a lower level of impurities (0.0 g/h of acetaldehyde and 2.0 g/h of formaldehyde) than the prior art (0.3 g/h of acetaldehyde and 4.6 g/h of formaldehyde).

The secondary components removed from the system by the process of the invention are 1.1 g/h of acetaldehyde and 0.7 g/h of formaldehyde in stream 25 and 1.6 g/h of acetaldehyde and 1.4 g/h of formaldehyde in stream 27 compared with only 1.2 g/h of acetaldehyde and 0.6 g/h of formaldehyde in stream 25 according to the prior art process.

We claim:

1. A process for distillative recovery of monoethylene glycol comprising hydrolyzing ethylene oxide with water to form a hydrolysis product stream and passing the hydrolysis product stream through a system comprising a battery of pressure dewatering columns, each having a feed point for introducing the hydrolysis product stream, and between each of which the hydrolysis product stream passes as an overhead stream, subsequent to the pressure dewatering columns, at least one vacuum dewatering column, and subsequent to the vacuum dewatering column, at least one column for purifying distillation, wherein at least the first pressure dewatering column of the battery has a stripping section with at least one separating stage, and wherein a portion of the overhead stream containing secondary components of at least the first pressure dewatering column having a stripping section is removed from the system, and wherein the stripping section has from 2 to 10 separating stages.

2. A process as claimed in claim 1, wherein the temperature of the first pressure dewatering column of the battery below the feed point is above 80° C., and the pressure in the stripping section is not less than 1 bar.

3. A process as claimed in claim 2, wherein the temperature is within the range from 100° C. to 250° C.

4. A process as claimed in claim 2, wherein the temperature is within the range of from 115° C. to 230° C.

5. A process as claimed in claim 2, wherein the pressure in the stripping section is within the range of from 2 to 30 bar.

6. A process as claimed in claim 1, wherein the portion of the overhead stream of the least first pressure dewatering column have a stripping section is introduced into a partial condensor and/or a stripper, and a gaseous stream enriched with the secondary components is removed from the stream.

7. A process as claimed in claim 6, wherein the stripper is a steam stripper.

8. A process as claimed in claim 6, wherein the partial condensor and/or the stripper re operated at above 90° C.

9. A process as claimed in claim 8, wherein the partial condensor and/or the stripper are operated at from 120° C. to 250° C.

10. A process as claimed in claim 1, wherein the stripping section has from 3 to 6 separating stages.

11. A process as claimed in claim 1, wherein all of the pressure dewatering columns have a stripping section with at least one separating stage.

12. A process as claimed in claim 1, wherein a portion of each overhead stream of the pressure dewatering columns having a stripping section is removed from the system.

* * * * *

UNITED STATES PATENT AND TRADEMARK OFFICE
CERTIFICATE OF CORRECTION

PATENT NO.    : 6,514,388 B1
DATED         : February 4, 2003
INVENTOR(S)   : Adrian et al.

It is certified that error appears in the above-identified patent and that said Letters Patent is hereby corrected as shown below:

Column 8,
Line 21, "of the least" should be -- of the at least --.
Line 28, "stripper re" should be -- stripper are --.

Signed and Sealed this

Twenty-seventh Day of May, 2003

JAMES E. ROGAN
*Director of the United States Patent and Trademark Office*